(12) United States Patent
Tovena-Pecault et al.

(10) Patent No.: US 7,878,078 B2
(45) Date of Patent: Feb. 1, 2011

(54) SAMPLING AND TRANSPORT DEVICE AND METHOD

(75) Inventors: Isabelle Tovena-Pecault, Leognan (FR); Patrick Manac'h, Salles (FR); Stéphanie Palmier, Bordeaux (FR)

(73) Assignee: Commissariat a l'Energie Atomique, Paris (FR)

( * ) Notice: Subject to any disclaimer, the term of this patent is extended or adjusted under 35 U.S.C. 154(b) by 436 days.

(21) Appl. No.: 11/919,378

(22) PCT Filed: Apr. 28, 2006

(86) PCT No.: PCT/FR2006/050400

§ 371 (c)(1), (2), (4) Date: Oct. 25, 2007

(87) PCT Pub. No.: WO2006/117494

PCT Pub. Date: Nov. 9, 2006

(65) Prior Publication Data

US 2009/0277284 A1   Nov. 12, 2009

(30) Foreign Application Priority Data

May 3, 2005   (FR) .................................. 05 51161

(51) Int. Cl.
*G01N 1/22* (2006.01)
(52) U.S. Cl. .................................. 73/863.22
(58) Field of Classification Search ............... 73/863.22
See application file for complete search history.

(56) References Cited

U.S. PATENT DOCUMENTS

| | | | |
|---|---|---|---|
| 3,897,688 A | | 8/1975 | Meserol et al. |
| 4,771,642 A | * | 9/1988 | Parth et al. ............... 73/863.52 |
| 5,009,646 A | * | 4/1991 | Sudo et al. ................... 604/230 |
| 5,212,991 A | * | 5/1993 | Suzanne et al. .............. 73/23.2 |
| 5,554,537 A | | 9/1996 | Sharpe |
| 5,965,453 A | * | 10/1999 | Skiffington et al. ......... 436/165 |
| 2001/0028664 A1 | * | 10/2001 | Vogler et al. ........... 372/29.011 |

FOREIGN PATENT DOCUMENTS

WO   WO 96/09527   3/1996

OTHER PUBLICATIONS

Japaneese Publication No. 2001336539, Dec. 7, 2001, Ito et al.*
ISO 14644-1.

* cited by examiner

*Primary Examiner* — Hezron Williams
*Assistant Examiner* — Alex Devito

(57) ABSTRACT

A device (1) for sampling particle contaminants is described. It may be adapted to a multitude of closed enclosures and with it, contaminants and/or pollutants present in the atmosphere of the enclosure may be recovered at a surface. With this sampling method, it is possible to obtain specific information as regards their behavior.

In particular, the sampling device (1) comprises a support (2) on which suitable substrates (6) may be positioned, with which samples may be collected. The device (1) is conformed so as to confine the taken samples until the site of the analysis in order to further increase the specificity of the measurement.

17 Claims, 1 Drawing Sheet

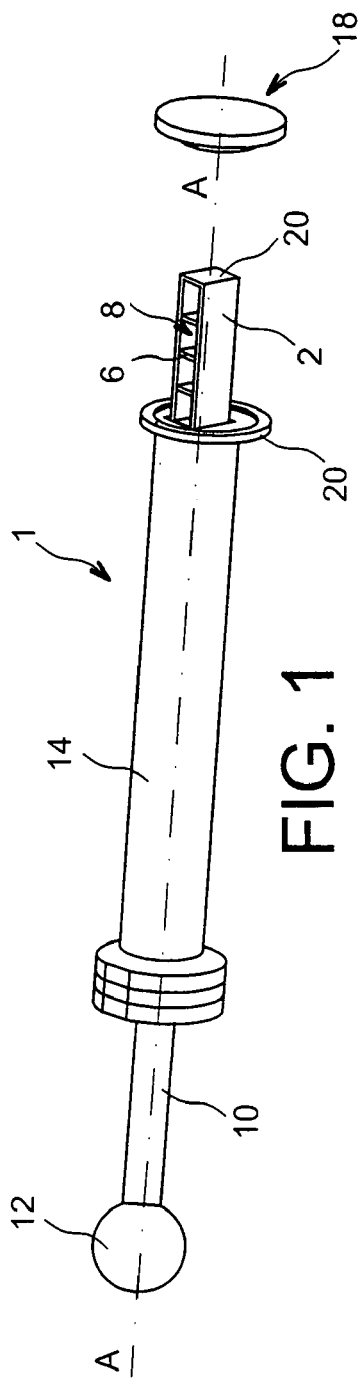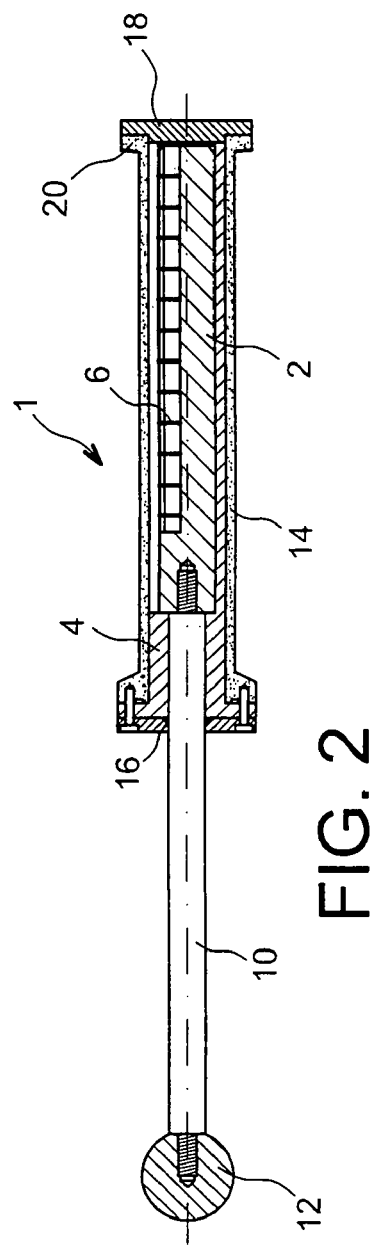

SAMPLING AND TRANSPORT DEVICE AND METHOD

TECHNICAL FIELD

The invention is located in the field of measurement, and more specifically of sampling before analysis.

In particular, the invention relates to a device which allows particle, molecular and biological contaminants to be collected notably in closed environments, and with which the sample may also be confined and transported, in order to obtain an analysis representative of the different pollution sources initially present in the controlled environment.

The invention also relates to a method of surface collection of aerosols present in a closed space.

STATE OF THE ART

Particle contaminants, also called aerosols, are solid particles suspended in a gaseous atmosphere (air or other gases). They may be characterized by their nature, by their size distribution (from a few fractions of nanometers to a few hundreds of microns) and their concentration per unit volume.

In the case of closed industrial environments, the contamination or dust volume level is specified according to classes of cleanliness, as referenced in the ISO 14644-1 standard; the ISO 14698 standard is used in the case of biological contaminants. Measurement methods are required in order to compare and classify the relevant medium, however standardization of these methods is only relative.

Generally, information concerning the level of contamination and dust of clean rooms and related controlled closed environments is obtained by means of particle counters or counters with condensation cores. However, the use of such equipment only gives information on the volume contamination of the enclosure and does not allow determination of the origin and behavior of the particles; morphological and chemical characterizations also prove to be necessary in order to evaluate cleanliness.

For example, the number of particles in a certain sampled gas volume may be obtained with an optical counter of particles: these particles generate diffusion and/or absorption of light, which may then be related to the size of the particles. However, this approach is usually based on assimilating the shape of the particles to a sphere, and does not take into account the optical behavior of the particles caused by their physico-chemical nature, for example absorption of light because of their composition.

Moreover, with dynamic pumping systems, measurements of contaminants present in the environment may be carried out. These measurements however refer to the volume sampled, generally in a central way, from a perturbed environment in terms of cleanliness and aeraulics by the simple presence of the pumping and generated flux.

Now, in many methods, it is actually the behavior of the aerosol contaminants at the surface of the manufactured products which is predominant: the goal is to obtain a material with in particular a surface composition as clean as possible. Specific information as regards the interaction between the surface of a product and the aerosol particles is thus desirable.

Accordingly, there is a need for optimizing the sampling of the contaminants in a closed enclosure, and allowing their analysis without altering them.

DISCUSSION OF THE INVENTION

The main object of the invention is to overcome the drawbacks of the existing sampling devices.

The invention in one of its aspects, relates to a sampling device which may be adapted to a plurality of enclosures, allowing contaminants and/or particle pollutants present in the surrounding atmosphere to be recovered. Sampling is carried out at the surface, by sedimentation on defined substrates, in order to best fit to the actual behavior of the particles.

Advantageously, the device for sampling the contaminants is compatible with the environment to be tested in terms of cleanliness; in particular, when the environments observe dust levels as defined in the ISO 14644-1 standard, the device does not provide any particle pollution capable of infringing the initial or required threshold. With it, it is possible to obtain a surface pollution condition of the materials by means of a (local) collection of various contaminants by sedimentation on suitable substrates, the contaminants not yet being deposited on a surface upon sampling. By analyzing the samples (substrate and/or collected contaminant), it will be possible to characterize the contaminants and to identify the source and noxiousness thereof; with the device of a preferred embodiment, it is further possible to confine the substrate and the picked-up sample until the site of the analysis in order to preserve the integrity of the sample.

The invention also relates to a method with which these aspects may be applied. In particular, the preferred method comprises the sealed connection between an enclosure and a sampling device, so that the atmosphere of the enclosure is not changed. According to the invention, the method then comprises the introduction of sampling substrates localized in the device, by sliding them, towards the inside of the enclosure, for a more or less long exposure time of the substrates and of the atmosphere of the enclosure, and then the sliding of the substrates so that they are sealably kept in the device, followed by the disconnection between the device and the enclosure. The analysis of the substrates at the surface of which the pollutants have been collected, may be carried out immediately or preferably by keeping them for the required time inside the device in a confined way, so that they are not altered.

A particularly suitable device thus comprises a support provided with means for placing sampling substrates which slide in and out of an envelope. Advantageously, the sliding does not generate any contaminating debris by selecting materials which are low generators of particles, for example because of their friction coefficient; both of them may thus be in Teflon™. Sliding is preferably assisted by connecting, either removably or not, the support with a handling rod and a grip handle.

The support/envelope assembly may be integrated to a body, for example a metal body, firmly attached to the envelope and allowing relative movement of the support. Preferably, the casing or body is made so as to define a sealed or hermetically sealed interior by the presence of gaskets and/or lid forming components. Advantageously, the body is provided at the end for the passage of the support with a standardized end piece providing a sealed connection with another end piece.

The design of the device thus provides very good insulation with regard to the outer atmosphere of the environment to be controlled, as well as a sealed confinement after disconnecting the device.

The support may have a rectangular or square section, and comprise a housing opening out on a side wall as a placement means. The support may preferably be provided with horizontal and/or vertical, and/or oblique notches relatively to the bottom of a cavity so that standardized substrates may be positioned therein, for example plates with dimensions 1×1 cm (±10%).

SHORT DESCRIPTION OF THE DRAWINGS

The features and advantages of the invention will be better understood upon reading the description which follows and with reference to the appended drawings, given as an illustration and by no means limiting.

FIG. 1 illustrates a device according to a preferred embodiment of the invention in the sampling position.

FIG. 2 illustrates the device of FIG. 1 in a sectional view and in a confinement position.

DETAILED DISCUSSION OF PARTICULAR EMBODIMENTS

The sampling device according to the invention provides collection of particle contaminants by sedimentation in a closed medium, allowing analysis by a static measurement of the deposited contamination.

The contaminants are collected on sampling substrates, inserted into the medium to be analyzed and then confined in the sampling device. Consequently, the result is representative of the deposit on the relevant sensitive surfaces but it does not stem from sampling by transfer from a surface where it would have been deposited beforehand. In particular, the absence of any dynamic pumping avoids perturbing the measurement, at notably cleanliness and aeraulics levels.

As illustrated in FIGS. 1 and 2, a sampling and confinement device 1 according to a preferred embodiment of the invention, comprises a sampling support 2 which may slide in and out of an envelope 4. The support 2 is longitudinal, extending along the sliding axis AA; advantageously, the support 2 has a quadrilateral, preferably rectangular or square, radial section. The envelope 4 is of a size and shape adapted to the support 2; the support 2 may assume a confinement position in which it is inside the envelope 4; the support 2 may slide towards a sampling position in which it is partly outside its envelope 4. Advantageously, the sliding is carried out without any friction generating particles between the support 2 and the envelope 4: their materials are suitably selected with notably a low friction coefficient; preferably the surface in contact between the support 2 and the envelope 4 is of the same composition. Consequently, it is preferable that the number of generated debris by the sliding be a minimum, and especially that their possible nature be as less a nuisance as possible with regard to the taken samples, so as to be able to distinguish them rapidly and remove them during the analysis. In particular, it is desirable that when they comply with a threshold as regards cleanliness, for example a dust rate criterion as defined in standards such as the ISO 14644-1 standard, the environments from which sampling is carried out, should not be polluted by particles which would cause them to exceed this threshold. Preferably, the envelope 4 and the support 2 are in Teflon™, in particular for sampling contaminants of the metal type.

The sampling support 2 allows the sampling substrates 6 to be positioned. Advantageously, such substrates 6 are removable for the analysis to be carried out; conventionally, these are square plates with a side of the order of 1 cm (0.9 to 1.1 cm) and of a thickness of the order of a millimeter, of mineral, organic or cellular nature (biofilm collection according to the ISO 14698 standard, for example). The sampling substrates 6 are selected depending on the components to be sampled and depending on the associated surface treatment, as well as on the type of desired characterization. For determining the size and the nature of the contaminants, the sampling substrates 6 may for example be carbonaceous adhesives; for the characterization of the interfaces between a determined sensitive material such as a silicon surface and contaminants in terms of adhesion, the substrates 6 may consist of this determined material and of the possible associated surface treatment.

Advantageously, the sampling support 2 is provided with means 8 for placing several substrates 6, of identical or different natures, on the same support 2 and therefore allowing several measurements to be conducted simultaneously. In a preferred embodiment, the means for positioning the substrate comprise at least one machined housing 8 in the support 2, for example on a wall of the support 2, with a rectangular, square or circular section, extending along the sliding axis AA: the substrate 6 may be positioned in the housing 8, vertically or horizontally, for example. Advantageously, the housing 8 is provided with notches provided for this purpose: preferably in pairs, notches on the side walls of the housing 8 resulting from the machining in the bulk of the support 2, guarantee that a substrate 6 is maintained in its position, for example in an oblique or perpendicular position relatively to the AA axis within the housing 8, in particular when setting the sampling position in the enclosure to be controlled. Various configurations of the positioning means and/or of the position of the substrate 6, may be combined on a same support 2.

The envelope 4 may be in a tubular form, i.e. with a cavity in which the support 2 in its retracted position is entirely localized. The envelope 4 may also comprise a cavity opening out laterally towards the housing 8 for positioning the substrates 6. The distal end of the support 2 is solid and adapted to the distal aperture of the envelope 4, so that, when the support 2 is retracted in its envelope 4, the latter aperture is blocked: for examples the envelope 4 is provided with a hole of square section adapted to the section of the support 2 and having a flared portion at its distal end, a flared portion in which the complementary distal end of the support 2 will be housed.

The other end of the support 2 may be firmly attached, preferably in a removable way, for example by a connection of the screwing type, to a handling rod 10 connected to a grip handle 12, thereby facilitating the sliding maneuvers of the support 2 relatively to its envelope 4. The proximal end of the envelope 2 is in this case provided with an aperture of a larger diameter than that of the rod 10, providing an easy slide.

In order to optimize the analysis, it is desirable that the sampling be carried out with as less influence as possible on the relevant environment. For closed spaces of the glove box type or inside a manufacturing apparatus, conventionally provided with means for communicating outwards, means are provided on the sampling device 1 in order to connect it in a hermetic sealed way.

The device 1 thus comprises a longitudinal casing or body 14, containing the envelope 4, advantageously firmly attached to it. The hollow preferably cylindrical body 14 is also used for handling the envelope and the support by means of a more robust structure: advantageously, the casing 14 is in metal, for example in stainless steel.

The body 14 is adapted so that the sampling support 2 may slide outwards. The proximal end portion of the box 14 may thus be provided with an aperture for letting through the handling rod 10. Advantageously, this aperture is provided with a gasket 16, which may for example be an O-ring and/or crushed by a <<compression gland>> system. In this case, the proximal aperture of the envelope 4 may be of much larger dimensions than the rod 10, and no joint is placed thereon: the sealed confinement of substrates 16 may be provided by the hollow body 14. With this embodiment, frictions between the rod 10 and the envelope 4 and possibly generated debris may be reduced.

At its distal end, having an aperture for letting through the support 2, the body 14 is preferably associated with a removable lid, for example a plug 18: once the sample is taken and the support 2 is in its confinement position, it is possible to block the end of the casing 14 by screwing in or fitting the plug 18 so as to transport the device 1. Such a lid may also be provided for the distal end of the body if the handle 12 and handling rod 10 are removable and withdrawn in order to transport the sample, so as to gain space, and to reuse the handle 10, 12 on another device for example.

To provide a sealed connection between the confined environment to be analyzed and the sampling device 1, the distal end of the body 14 is advantageously provided with an end piece 20 by which it is attached onto the communication means of the enclosure to be tested. Preferably, the end piece 20 forms the distal end of the body 14 and is in the form of a standardized interface; for example, the end of the body 14 is an end piece 20 of the DN40 type from vacuum technology: such an end piece, similar to a crushed gasket, may be connected in a standardized and vacuum-compatible way onto suitable communication means.

It is thus possible to connect the device 1 according to the invention in accordance with a standardized procedure to a closed space provided with the corresponding end piece and in which the sampling should be carried out: the seal of the system consisting of the device 1 and of the closed enclosure is then provided without any perturbation of the inner atmosphere. The support 2 is then introduced by sliding it into the enclosure and out of the body 14/envelope 4 assembly in order to carry out sampling on the substrate 6 and collect the aerosols, without altering the environment by a selection of materials which only generate a little debris when sliding relatively to each other. At the end of the sampling, the support 2 provided with substrates 6 on which the samples of particles have settled, is reintegrated by sliding into the envelope 4, at least a partial seal is obtained when disconnecting the end piece 20 from the communication means by the matching between the distal ends of the support 2 and of the envelope 4. If this is desired, the seal may then be optimized by placing the plug 18: once the samples have been taken, it is thereby possible to keep them away from external contaminations until the analysis, which may be carried out away from the sample, both in localization and in duration, without altering the result.

Advantageously, the device 1 according to the invention may be entirely dismantled: in particular, the sampling support 2 may be completely disassociated from its envelope 4, itself being removable relatively to the external body 14. With this embodiment, it is possible to clean the assembly of the device 1 if necessary, and this extensively and adapted to each of the materials forming the different components. Compatibility of the device 1 with the most demanding cleanliness classes (from class ISO 4) may thereby be provided.

Moreover, this dismantling also allows a same handle 10, 12, a same casing 14, or even a same envelope 4, to be used for interchangeable sampling supports 2 and selected depending on the desired use and the relevant substrates 6.

Different components of the device 1 according to the invention may be made in different suitable materials; advantageously, the materials are neutral as regard to the environment in which the device 1 may be localized and do not change the dust levels, notably when it complies with a standard of the relevant environment. Preferably, the internal surfaces of the device 1 and notably of the housings 8 have minimum physico-chemical adsorption properties in order to provide selective connection of the contaminants on the sampling substrates 6 and not on the actual support 2.

The device 1 according to the invention therefore groups three tools together into one as this is both a tool for sampling contaminants, a tool for confinement and a tool for transporting samples: once taken, the samples may be stored on the substrate 6 and in the envelope 4 for their transport, the device 1 not requiring any complementary handling or conditioning equipments. The sampling substrates 6 comprising the taken samples on their surface may be analyzed immediately or after a more or less long transport time towards different measurement apparatuses.

The substrates 6 firmly attached to the support 2 and confined in the body 14 of the device 1 may be extracted on the site of the analysis by sliding towards the outside of the envelope 4, according to a procedure similar to the sampling one. In particular, the samples may therefore be characterized by any suitable physico-chemical method (scanning electron microscopy, possibly associated with an MEB-EDS X-ray probe; infrared spectroscopy, possibly via Fourier transform (FTIR); . . . ) in order to determine the different characteristics of interest (nature, amount of contaminants, . . . ), without any constraint relatively to the sampling site.

It is considered that in order to obtain reliable results, substrates 6 with a surface of the order of one cm$^2$, or even more, are desirable for a reasonable exposure time. In order to obtain an adequate number of simultaneous samples, in particular twelve samples, a preferred embodiment comprises an axisymmetric cylindrical stainless steel body with a diameter between 40 and 50 mm, for example 45 mm, for an overall length of 300-350 mm (i.e. taking the end portions into account), for example 320 mm. With this embodiment, it is possible to have maximum bulk (distal end of the device 1 up to the handle 12) less than 550 mm so that samplings may be carried out on all the closed enclosures, around which a space of one meter is customary. Further, because of its relative lightweight (less than 35 kg), of its handling capacity and of: its robustness (stiffness, impact strength), the device 1 may easily be used and transported without any risk of degradation of the samples. Moreover, as it does not require any energy or fluids (gases or liquids) in order to operate, it may be used in very isolated sites.

The device according to the invention may be used in all the fields of science and industry in which aerosols may have an influence. In particular, it is possible to apply the device according to the invention to rooms and environments with controlled dust levels, for example according to the ISO 14644-7 standard, such as clean rooms and the related separative enclosures (clean air station, glove box, isolators and <<mini-environments >>). The relevant fields in particular include optics, laser, aerospace, electronics, integrated circuits, agri-food, pharmacy, nanotechnology in particular of powders, medical and hospital environments, . . .

Compatible in terms of contamination with the enclosure to be tested, the sampling device according to the invention does not generate per se any breaking of the cleanliness chain inside the closed environment, neither in the inside of the actual device. By selecting the materials, when designing and assembling the whole, the risk of intrinsic pollution of the device is quasi-zero with respect to the environment and to the samples (minimization of a potential background noise): generation of particle and molecular pollutants (by desorption, for example) is minimal.

The invention claimed is:

1. A device for sampling particles comprising an elongated sampling support provided with housing means having a cavity on one side thereof for removably positioning at least one sampling substrate in the support, a longitudinal envelope surrounding the support to permit relative sliding contact engagement between the envelope and the support along a longitudinal axis through the device such that the support is able to slide in engaging contact with the envelope between a first sampling position in which the support extends outside the envelope, and a second position in which the support is confined to within the envelope with the support and the envelope consisting of materials having a low friction coefficient such that particle dust, if any, generated by sliding engagement between the envelop and support, is limited so that sampling is not changed by dust pollution from sliding engagement between the support and envelope; a handling rod connected to the proximal end of the support for manually controlling sliding movement of the support relative to the envelope, a gasket connected at the proximal end of the envelope for sealing the handing rod and envelope at its proximal end and connection means for sealing the distal end of the device when the support is confined to within the enclosure.

2. The device according to claim 1 wherein the support and envelope are composed of polytetraflouroethylene.

3. The device according to claim 1 wherein the support has a rectangular radial section.

4. The device according to claim 1 wherein the positioning means comprise at least one machined housing in the support, extending along the axis.

5. The device according to claim 4 wherein the positioning means comprise at least one notch on an internal wall of the machined housing.

6. The device according to claim 5 wherein each notch is doubled in machined pairs in the bulk of the support so as to allow insertion into the pair of notches, of a substrate forming an angle relatively to the axis of the device, in particular equal to 90° or 180°.

7. The device according to claim 6 wherein the housing has a square radial section with the side between 0.9 and 1.1 cm, and the pairs of notches are perpendicular to the axis.

8. The device according to claim 1, comprising a body firmly attached around the envelope, with the distal end of the body being provided with an aperture for the passage of the support.

9. The device according to claim 8 wherein the distal aperture of the body comprises said connection means.

10. The device according to claim 9 wherein the connection means are an end piece of the DN40 type.

11. The device according to claim 8 further comprising a removable plug capable of sealably blocking the distal aperture of the body to seal the body and device from the atmosphere.

12. The device according to claim 8 wherein the proximal end of the body comprises means so that the body forms a sealed enclosure around positioning means.

13. The device according to claim 12 wherein said gasket is an O-ring located at the proximal end of the body capable of letting said handling rod sealably slide through it.

14. The device according to claim 8 wherein the body is composed of a metal.

15. The device according to claim 1 wherein the proximal end of the support comprises a threaded portion, and the proximal end of the envelope comprises an aperture facing the threaded portion.

16. The device according to claim 15 wherein said handling rod is screwed to the threaded portion of the support to assist its sliding.

17. A method for collecting an aerosol contaminant in a closed environment provided with communication means comprising:

connecting on the communication means, a sampling device comprising an enclosure provided with an end piece adapted to the communication means and a support provided with at least one sampling substrate sliding inside the enclosure; wherein the enclosure includes an elongated envelope arranged in sliding engagement with the support to enable the support to slide in contact engagement with the envelope along the longitudinal axis of the device between a first sampling position in which the sampling substrate in the support is exposed outside the envelope, and a second position in which the support is confined to inside the envelope and having a body engaged to the envelop to which the end piece is affixed at the distal end of the body;

introducing the support of the device inside the closed environment;

collecting the contaminant on the sampling substrate;

sliding the support so that the sampling substrate and the collected contaminant are confined to the position within the envelope;

selecting a material composition for the support and for the envelope of a low friction coefficient such that particle dust, if any, generated by sliding contact engagement between the support and envelope will be limited so that sampling is not changed by dust pollution from sliding engagement between the support and envelope;

disconnecting the end piece from the communication means; and affixing a plug to the end piece to seal the device from the environment.

* * * * *